United States Patent [19]

Rand et al.

[11] Patent Number: 4,618,970
[45] Date of Patent: Oct. 21, 1986

[54] BEAM POSITIONING ARRANGEMENT FOR USE IN A SCANNING ELECTRON BEAM COMPUTED TOMOGRAPHY SCANNER AND METHOD

[75] Inventors: Roy E. Rand, Palo Alto; John W. J. Mitchell, Redwood City; John L. Couch, San Francisco, all of Calif.

[73] Assignee: Imatron, Inc., San Francisco, Calif.

[21] Appl. No.: 597,134

[22] Filed: Apr. 5, 1984

[51] Int. Cl.$^4$ .......................... A61B 6/08; H01J 35/14
[52] U.S. Cl. ..................................... 378/10; 378/205; 378/119; 378/138; 378/137
[58] Field of Search ...................... 378/10, 12, 16, 19, 378/205, 113, 137, 138; 250/491.1

[56] References Cited

U.S. PATENT DOCUMENTS

| | | | |
|---|---|---|---|
| 4,075,489 | 2/1978 | Neal et al. | 378/113 |
| 4,243,888 | 1/1981 | Gruhn et al. | 250/491.1 |
| 4,352,021 | 9/1982 | Boyd et al. | 378/12 |

*Primary Examiner*—Craig E. Church
*Assistant Examiner*—Charles F. Wieland

*Attorney, Agent, or Firm*—Flehr, Hohbach, Test, Albritton & Herbert

[57] ABSTRACT

A scanning electron beam computed tomography scanner is disclosed herein and includes means defining a vacuum chamber, means for producing an electron beam at a first location in the chamber and for directing the beam to a second location therein along a particular desired path. A target of a type which produces X-rays as a result of the impingement thereon by the electron beam is positioned at a third location and means at the second location are provided to cause the beam to impinge on the target in a scanning fashion for producing X-rays. The scanner also includes a system for maintaining the electron beam on the desired path between the first and second locations. To this end, the system includes first means acting on the beam between these locations so as to detect for deviations, if any, between the actual path taken by the beam and the desired path and means responsive to these deviations, again if any, for adjusting the position of the electron beam in order to eliminate the deviations.

6 Claims, 5 Drawing Figures

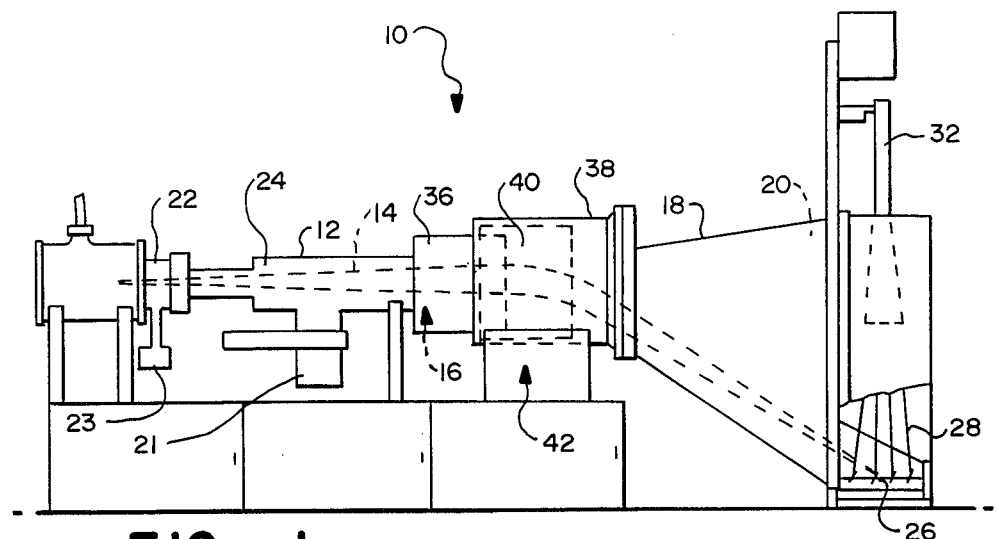
FIG.—1
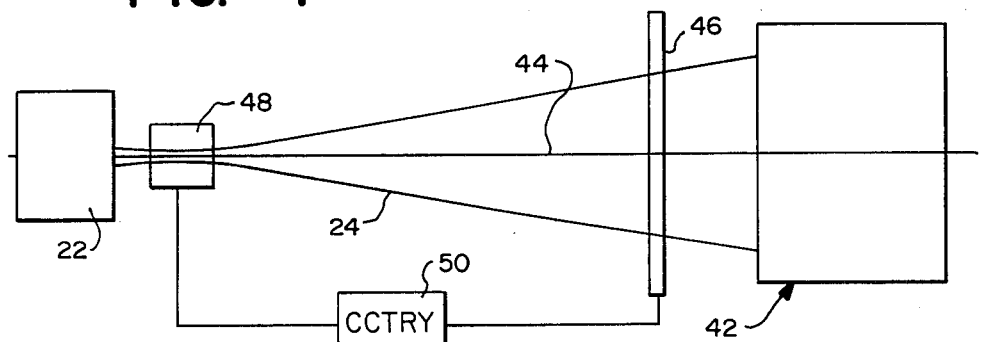
FIG.—2
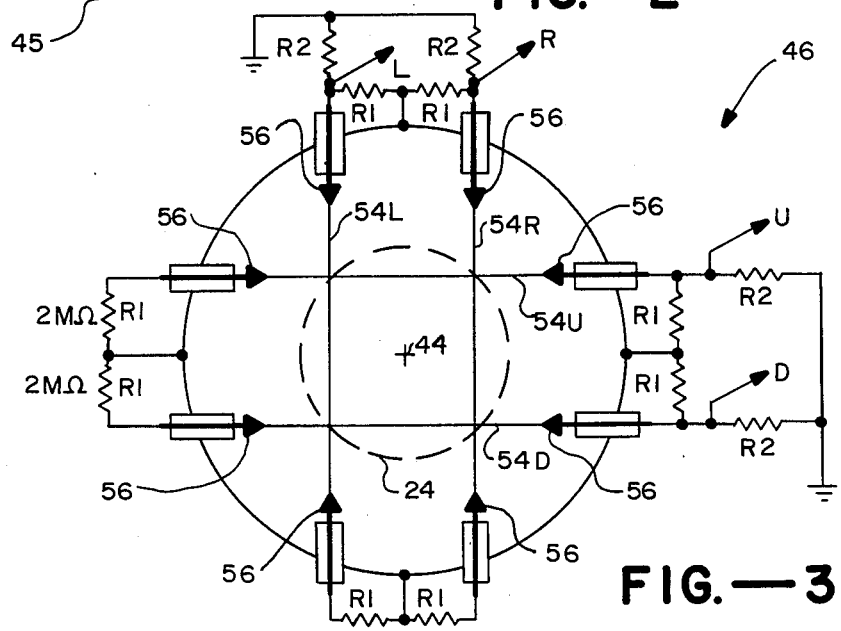
FIG.—3

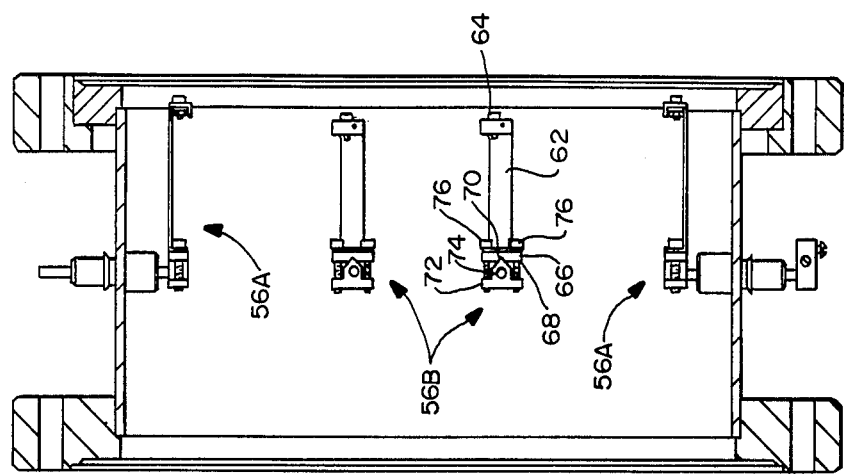
FIG.—5
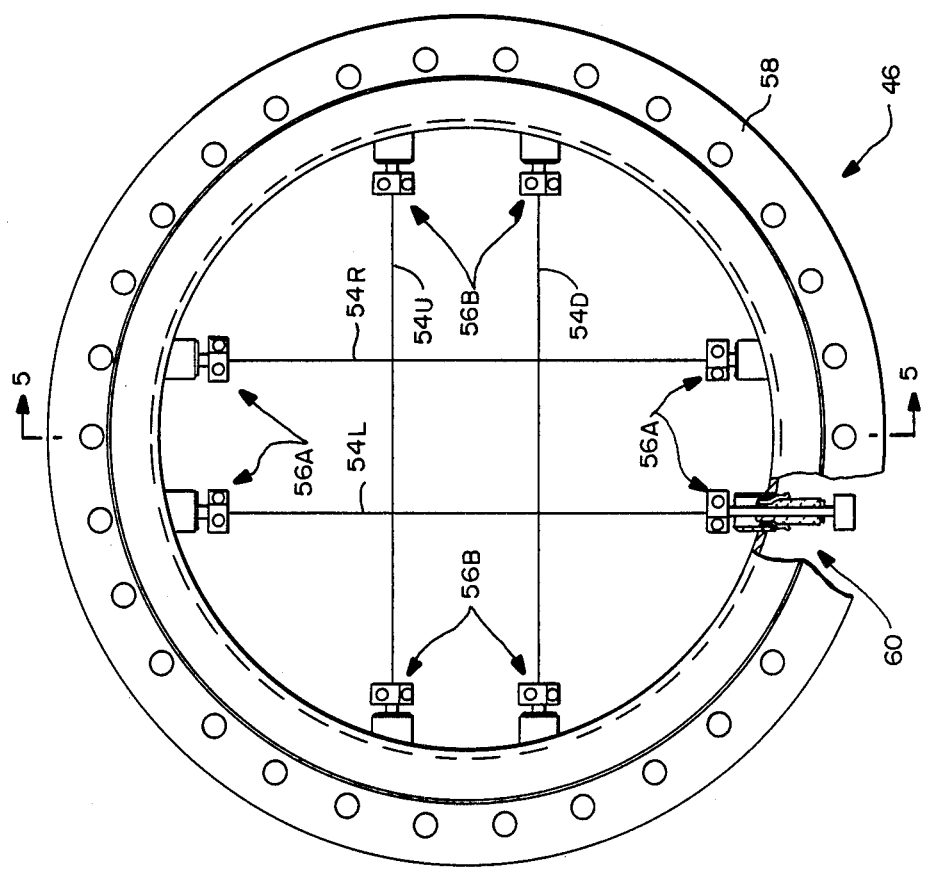
FIG.—4

BEAM POSITIONING ARRANGEMENT FOR USE IN A SCANNING ELECTRON BEAM COMPUTED TOMOGRAPHY SCANNER AND METHOD

The present invention relates generally to an apparatus such as a scanning electron beam computed tomography scanner in which an electron beam is directed from a first location to a second location along a specific desired path and more particularly to an arrangement for insuring that the electron beam takes the desired path.

In U.S. Pat. No. 4,352,021 (Boyd et al) and copending U.S. patent application Ser. No. 434,252, filed Oct. 14, 1982 and entitled ELECTRON BEAM CONTROL ASSEMBLY AND METHOD FOR A SCANNING ELECTRON BEAM COMPUTED TOMOGRAPHY SCANNER (hereinafter referred to as the "Rand" patent application), a scanning electron beam computed tomography scanner is disclosed and reference is made to this patent and patent application. The scanner described there includes means defining a vacuum chamber, means for producing an electron beam at a first location in the chamber and for directing the beam to a second location therein along a particular desired path. A target of the type which produces X-rays as a result of the impingement thereon by the electron beam is positioned at a third location and means are provided at the second location for focusing the beam onto the target in a scanning (deflecting) fashion for producing X-rays.

In the scanner of the type illustrated in the Boyd patent and Rand patent application, it is important that the electron beam enter the second location, that is, the location containing the focusing and deflecting means on-axis, that is, along the desired path referred to above, so that it does not collide with the vacuum chamber walls and the properties of the beam optical system are optimized.

In view of the foregoing, it is a primary object of the present invention to provide an uncomplicated means for and method of insuring that the electron beam discussed above does indeed remain on-axis, that is, on the particular desired path, as it enters the focusing and scanning means.

A more particular object of the present invention is to provide a specific, uncomplicated and yet reliable arrangement for detecting any deviations in the path taken by the electron beam from the desired on-axis path.

As will be described in more detail hereinafter, the present invention provides for first means acting on the above-recited electron beam between the first and second locations, preferably at the location of the focusing and deflecting means, so as to direct for deviations, if any, between the actual path taken by the beam and the desired (on-axis) path. At the same time, second means are provided for adjusting the position of the electron beam, if necessary, in response to any deviations, in order to eliminate the latter and thereby maintain the beam on the desired path.

In a preferred embodiment of the present invention, the first means recited immediately above includes an arrangement of electrically conductive wires located across the desired path of the electron beam such that the impingement of one or more of these wires by the electron beam produces an electrical signal dependent on the actual path taken by the beam. In this way, the second means recited above can be made responsive to this signal either automatically or via an operator for adjusting the position of the electron beam, if necessary, in order to eliminate any deviations between the actual path taken by the beam and the desired beam. In the case where the electron beam has a circular cross sectional configuration before entering the focusing and scanning means (which is typically the case), the signal providing arrangement of wires preferably includes four such wires positioned relative to one another and to the desired path so as to define the four sides of a square having its center at the center of the desired path, whereby the electron beam impinges on all four wires the same amount when the beam is on-axis.

The present invention will be described in more detail hereinafter in conjunction with the drawing, wherein:

FIG. 1 diagrammatically illustrates a scanning electron beam computed tomography scanner including a beam positioning system designed in accordance with the present invention;

FIG. 2 diagrammatically illustrates aspects of the scanner shown in FIG. 1 including specifically the beam positioning system;

FIG. 3 schematically illustrates an arrangement for detecting deviations in the actual path taken by the electron beam in the scanner illustrated in FIG. 1 from the desired beam path.

FIG. 4 illustrates a frontval view of an actual working embodiment of a part of the arrangement shown in FIG. 3; and FIG. 5 illustrates the part of the arrangement of FIG. 3 in side section, as taken along line 5—5 in FIG. 4.

Turning now to the drawings, attention is first directed to FIG. 1 which illustrates a scanning electron beam computed tomography scanner generally indicated by the reference numeral 10. With the exception of the present invention which will be discussed below, scanner 10 may be identical to the one described in the previously referred to Boyd et al patent and/or the Rand application. As illustrated in FIG. 1, scanner 10 includes a vacuum pipe generally indicated at 12 for defining one section 14 of a vacuum chamber 16, means generally indicated at 18 for defining a second section 20 of the same chamber, and a vacuum pump 21 acting on the chamber. Means including an electron gun 22 and its own vacuum pump 23 located at the rearwardmost end of chamber 16 serves to produce a space-charge limited electron beam 24 which is directed horizontally in a continuously expanding fashion through chamber section 14 to the forwardmost end of the latter where it is acted upon in the manner to be discussed below. The cross section of electron beam 24 between electron gun 22 and the forwardmost end of chamber section 14 is circular in configuration.

As illustrated in FIG. 1, means 18 defining chamber section 20 is configured to define a somewhat cone-shaped chamber section, at least to the extent that it tapers downward and outward from chamber section 14. At the forwardmot end of this chamber section, scanner 10 includes a set of targets of the type which produce X-rays 28 as a result of the impingement thereon by electron beam 24. A typical target 26 is generally arcuate in form and extends around the inside of chamber section 20 at its forwardmost end. A solenoid coil 36 and an assembly of dipole coils 38, the latter containing a set of magnetic guadrupole cells 40 also form part of scanner 10. These three components combine to provide an overall arrangement 42 at the forwardmost end of chamber section 16 and the rearwardmost end of chamber section 20 for focusing beam 24 onto one of the targets 26 and for causing the beam to scan (deflect) along the length of that target so as to provide X-rays 28.

The components making up overall scanner 10, as described thus far, form part of the previously recited Boyd et al patent and/or the Rand application and therefore will not be described herein. In this regard, it should be noted that scanner 10 may include other components (not disclosed herein) which do not form part of the present invention but which are necessary or desirable to operation of the overall scanner. For a discussion of these components, reference is again made to the Boyd et al patent and the Rand patent application.

As indicated above, it is important that electron beam 24 enter the focusing and scanning arrangement 42 on-axis which, in the embodiment illustrated, means along a central path through section 14 of vacuum chamber 16. FIG. 2 diagrammatically illustrates this axis at 44 which extends from the electron gun 22 to arrangement 42. In accordance with the present invention, the overall scanner 10 includes a system 45 designed in accordance with the present invention for insuring that beam 24 is maintained on-axis, that is, such that the axis of the beam remains in line with axis 44. System 45 includes a device 46 located across the desired beam path 44 between electron gun 22 and arrangement 42, preferably just upstream of or inside, arrangement 42 as illustrated, for detecting deviations, if any, between the actual path taken by the beam and axis 44. System 45 also includes a device 48 located immediately downstream of gun 22 for adjusting the position of beam 24, if necessary, in order to eliminate any deviations in the beam path, whereby to maintain the beam on-axis. In a preferred embodiment of the present invention, device 48 is comprised of steering coils which are responsive to electrical signals for controlling horizontal and vertical movement of the beam as it leaves the electron beam gun.

As will be seen hereinafter, arrangement 46 is configured to produce an electrical signal (actually a set of signals) dependant on the actual path taken by beam 24, as detected at device 46. Suitable electronic circuitry indicated generally at 50 and labeled CCTRX and forming part of the overall system 45 conditions this signal and otherwise acts on it so that it can be used to adjust device 48 such that the latter responds to any deviation in the path taken by the electron beam in order to eliminate that deviation and thereby maintain the beam on-axis. The device 48 per se and the circuitry generally indicated at 50 do not form part of the present invention, and, hence, will not be discussed any further herein. It suffices to say that one with ordinary skill in the art can readily provide both in view of the teachings herein.

Turning specifically to FIG. 3, attention is directed to device 46 which is designed in accordance with the present invention. This device is shown including four electrically conductive wires 54L, 54R, 54U, and 54D which are supported by a network of suitable tensioning and adjusting devices 56 which are attached to electrical feed-throughs in vacuum pipe 12. These wires are arranged relative to one another so as to define the four sides of a square having its center coextensive with axis 44, as illustrated in FIG. 3. Each end of each wire is preferably grounded to the vacuum pipe 12 by means of a suitably sized resistor R1. This provides spark protection even if the wires break. The continuity of the wires in the pipe may be checked by measuring the resistance between pairs of feed-throughs. As will be discussed below, upon impingement of these wires by beam 24, current is produced in the wires so impinged. Most of this current passes through suitably sized resistors R2 to ground. The voltage developed across these resistors is directed via cooperating terminals, e.g. the terminals L, R, U, and D to sample and hold circuits forming part of circuitry 50, as will also be discussed below.

Having described the device 46, attention is now directed to the way in which it operates to detect for deviations in the actual path taken by beam 24 from the desired path. First, let it be assumed that the beam is on-axis, as illustrated in FIG. 3. It will also be assumed that the beam has a uniform current density. Under these circumstances, each wire 54 is impinged on by beam 24 in exactly the same way as the other wires. As a result, the same amount of current is produced in each wire and therefore all of the signals at terminals L, R, U, and D will be equal. These equal signals are compared and acted on by circuitry 50 to operate device 48. In this case, because the four signals are equal, indicating that the beam 24 is on-axis, it is not necessary for device 48 to change the position of the electron beam and therefore it is not necessary to provide any signals to device 48 from circuitry 50. On the other hand, let it be assumed that the beam is not on axis but rather, for example, slightly above axis and slightly to the right of axis, as viewed in FIG. 3. In this case, more of wire 54U is impinged on by the beam than wire 54D and more of wire 54R is impinged on by the beam than wire 54L. As a result, the voltage signal out of terminal U is greater than the signal out of terminal D and the signal out of terminal R is greater than the signal out of terminal L. These signals are compared by circuitry 50 which may include a computer which, in turn, produces responsive output signals for operating device 48, specifically the steering coils discussed above, in order to cause the beam to move back to its on-axis position which occurs when all of the signals are again equal.

From the foregoing discussion of device 46 above, it should be apparent that the various output signals from terminals L, R, U, and D depend upon exactly how beam 24 impinges the four wires 54 and that these signals can be used to operate device 48 in order to maintain the beam on-axis. In an actual working embodiment, each of the wires 54 is a tungsten wire which is 0.375 mm in diameter. Each of the resistors R1 is a two Mohm resistor and each of the resistors R2 is a two kohm resistor. A typical electron beam of 600 mA current would have a diameter of about .8 cm at the monitoring point, that is, at device 46. The wires 54 are spaced 6 cm apart. Thus, for a properly centered beam, 5.3 cm of each wire is in the beam. Assuming uniform current density, as stated previously, the fraction of the beam current interrupted by each wire is only 0.004. Therefore, it should be apparent that device 46 does not interfere with the operation of overall scanner 10. Under these conditions, assuming a secondary emission coefficient of 0.5 for tungsten, the current to each wire is 1.2 milliamps and the output signal to the sample and hold circuits forming part of circuitry 50 is 2.4 volts.

The foregoing was an actual operating embodiment of the device 46 designed in accordance with the embodiment illustrated in FIG. 3, that is, one having a network of wires which together form a square especially suitable for monitoring the position of an electron beam having a circular cross section. It is to be understood that the present invention is not limited to the embodiment illustrated or the actual working embodiment described. The particular configuration of wires making up the device will depend upon the cross section configuration of the beam being monitored. Moreover, it is to be understood that overall system 45 is not limited to the particular steering coils making up device 48 and circuitry 50 but any suitable means compatible with device 46 in order to maintain electron beam 24 on axis may be utilized as part of the overall system.

Referring now to FIGS. 4 and 5, attention is directed to an actual structural embodiment of device 46, excluding various resistors R1 and R2 and the output terminals L, R, U and D. As seen in these latter figures, the overall device includes a main support ring (a spool weldment) 58 which forms part of vacuum pipe 12 (not shown in FIG. 1) and which supports adjusting devices 56. With one exception to be discussed below, these latter devices are identical to one another. The four devices which connect the ends of wires 54L and 54R have been designated by the reference numeral 56A and those devices which connect the ends of wires 54U and D have been designated by the reference numeral 56B. Each of these devices includes a feed through mechanism 60, one of which is generally indicated in FIG. 4. Each of these mechanisms is identical to the others and serves as a pass-through (through the support ring) and as a means for electrically connecting one end of the corresponding wire to the corresponding resistor or resistors and output terminal illustrated in FIG. 3. These mechanisms do not per se' form part of the present invention.

Referring specifically to FIG. 5, each of the devices 56 is shown in side view. In accordance with the present invention, each of these devices includes an elongated electrically conductive arm 62 extending out from the inner end of an associated mechanism 60. Each of these arms is constructed of a spring-type material, for example spring steel, so as to act as the tension spring. Its free end includes fastening means generally indicated at 64 for physically connecting one end of a corresponding wire to the free end of spring arm 62. The other end of each spring arm is integrally formed with or otherwise connected to an enlarged base flange 66 having a back face 68 which contains a centrally located, generally V-shaped recess 70. A flange number 72 forms part of each device 56 and includes an outwardly projecting fulcrum 74 which cooperates with recess 70 such that base 66 is able to pivot to a limited extent about the tip of fulcrum 74 within a plane passing through the tip. The enlarged base 66 of each device 56 and its cooperating flange 72 include threaded openings for receiving a pair of adjustment screws 76 on either side of recess 70.

As indicated above all of the devices 56 are identical, with one exception. This exception is best illustrated in FIG. 5. Specifically, the spring arms of the devices 56A are slightly longer than the spring arms of devices 56B. In this way, the wires 54L and 54R are physically positioned across but in front of the wires 54U and 54D without touching one another.

Having described the various devices 56A and 56B structurally, attention is directed to the way in which these devices support the wires 54 in accordance with the present invention. First, because of spring arms 62, the wires can be maintained taught (in tension) throughout the overall operation of device 46 and can specifically take into account and accommodate for thermal expansion and contraction of the wires 54 during operation of device 46. Moreover, by adjusting the adjustment screws 76 of each device 56, the free end of its spring arm can be adjusted to a limited extent (horizontally in the case of devices 56A and vertically in the case of devices 56B). This, in turn, adjusts the horizontal and vertical positions of wires 54. Using the devices 56B as an example and referring to FIG. 5, by changing the relative positions of the adjustment screws 76, it can been seen that the free ends of spring arms 62 can be made to move toward one another or away from one another. This in turn moves the ends of wires 54U and 54D towards one another or away from one another (see FIG. 4) so as to precisely adjust the positions of these wires. In this regard, it is desirable to make the two wires parallel to one another and horizontal as possible and equidistant from the device axis, in a preferred embodiment. In the same manner, the devices 56A can be used to adjust the ends of wires 54L and 54R in order to make these wires parallel to one another and as vertical as possible and equidistant from the device axis.

What is claimed is:

1. In a scanning electron beam computed tomography scanner including means defining a vacuum chamber, means for producing an electron beam at a first location in the chamber and for directing said beam to a second location therein along a particular desired path, an arrangement for detecting deviations between the actual path taken by said beam between said first and second locations and the desired path, said arrangement comprising a network of electrically conductive wires which are electrically insulated from one another and which are located across said desired path between said first and second locations such that the impingement of one or more of said wires by said electron beam produces an electrical signal dependent upon the actual path taken by said beam between said locations, whereby said signal can be compared to a reference signal corresponding to one which is produced by said network of wires as a result of the impingement of said beam when the latter extends along said desired path, said scanner including means for comparing said first mentioned signal with said reference signal.

2. An arrangement according to claim 1 wherein said electron beam has a circular cross section between said first and second locations and wherein said network of wires includes four such wires positioned relative to one another and to said desired beam path so as to define the four sides of a square having its center at the center of said desired path, whereby said electron beam impinges on all of said four wires the same amount when the beam is directed along said desired path.

3. An arrangement according to claim 2 wherein each of said four wires includes means for producing its own separate sub signal dependent upon the way in which said beam impinges that wire, said four separate subsignals characterized the actual path taken by said beam.

4. An arrangement according to claim 2 wherein said arrangement includes means for fixedly holding each end of each of said four wires, each of said holding means including a spring mechanism such that the opposite ends of each of said wires is held in a state of tension.

5. An arrangement according to claim 4 wherein each of said holding means includes means for fixedly adjusting to a limited extent the position of the end of the wire held by that holding means within a given plane such that the ends of each pair of parallel wires making up said square where can be adjusted relative to one another and relates to the device axis.

6. An arrangement according to claim 1 wherein said network of electrically conductive wires includes means for holding opposite ends of each of said wires such that said wires are continuously maintained in tension, said holding means including means for adjusting the position of each end of each of said wires to a limited extent in a given plane, whereby all of the ends of all of the said wires can be adjusted relative to one another and related to the device axis.

* * * * *